(12) United States Patent
Park et al.

(10) Patent No.: US 12,150,806 B2
(45) Date of Patent: Nov. 26, 2024

(54) X-RAY DEVICE

(71) Applicant: POSKOM CO., LTD., Gyeonggi-do (KR)

(72) Inventors: Jong Rae Park, Seoul (KR); Ki Bong Sung, Gyeonggi-do (KR)

(73) Assignee: POSKOM CO., LTD., Gyeonggi-Do (KR)

( * ) Notice: Subject to any disclaimer, the term of this patent is extended or adjusted under 35 U.S.C. 154(b) by 77 days.

(21) Appl. No.: 17/848,401

(22) Filed: Jun. 24, 2022

(65) Prior Publication Data

US 2023/0041571 A1   Feb. 9, 2023

(30) Foreign Application Priority Data

Aug. 5, 2021   (KR) .......................... 10-2021-0103234

(51) Int. Cl.
   *A61B 6/58*   (2024.01)
   *A61B 6/00*   (2024.01)

(52) U.S. Cl.
   CPC .............. *A61B 6/589* (2013.01); *A61B 6/544* (2013.01); *A61B 6/545* (2013.01); *A61B 6/588* (2013.01)

(58) Field of Classification Search
   CPC .. A61B 6/10; A61B 6/508; A61B 6/54; A61B 6/588; A61B 6/589; A61B 6/544; A61B 6/542; A61B 6/545
   See application file for complete search history.

(56) References Cited

U.S. PATENT DOCUMENTS

| | | | |
|---|---|---|---|
| 2007/0140429 A1* | 6/2007 | Hoheisel ................. | A61B 6/08 378/117 |
| 2010/0329430 A1* | 12/2010 | Zeng ...................... | A61B 6/588 378/165 |
| 2011/0249793 A1* | 10/2011 | Lalena ................. | A61B 6/4266 378/62 |
| 2012/0027174 A1* | 2/2012 | Takamura ................ | A61B 6/54 378/62 |
| 2013/0121477 A1* | 5/2013 | Lee ....................... | A61B 6/4482 378/197 |
| 2014/0140477 A1* | 5/2014 | Richard ................. | A61B 6/544 378/62 |

(Continued)

FOREIGN PATENT DOCUMENTS

KR   10-2211183   2/2021

*Primary Examiner* — Dani Fox
*Assistant Examiner* — Soorena Kefayati
(74) *Attorney, Agent, or Firm* — Ladas & Parry, LLP (57) ABSTRACT

An X-ray device comprises: a radiator configured to radiate an X-ray; a distance measurement sensor configured to measure a value of a distance to an object; and a controller configured to acquire a first separation distance between an X-ray radiation focal point of the radiator and a subject, and control operation of the radiator based on the acquired first separation distance. Through these, the radiation of the X-ray can be prevented without a physical skin guard when the subject approaches within a certain distance from the radiator, thereby preventing the increase in the size caused by the installation of the physical skin guard, and a process of manually setting a strength of the X-ray radiation output according to the thickness of the subject can be omitted, thereby improving easiness of the X-ray imaging and reducing the time for the X-ray imaging.

8 Claims, 7 Drawing Sheets

(56) References Cited

U.S. PATENT DOCUMENTS

| | | | |
|---|---|---|---|
| 2015/0063538 A1* | 3/2015 | Stevenson | A61B 6/544 |
| | | | 378/55 |
| 2016/0089104 A1* | 3/2016 | Naito | A61B 6/4417 |
| | | | 600/449 |
| 2016/0287194 A1* | 10/2016 | Nariyuki | A61B 6/4411 |
| 2016/0374637 A1* | 12/2016 | Lee | A61B 6/54 |
| | | | 378/54 |
| 2017/0007196 A1* | 1/2017 | Don | A61B 6/461 |
| 2017/0112460 A1* | 4/2017 | Merckx | A61B 6/542 |
| 2018/0070911 A1* | 3/2018 | Franklin | A61B 6/487 |
| 2018/0303440 A1* | 10/2018 | Sung | A61B 6/4035 |
| 2019/0059829 A1* | 2/2019 | Han | A61B 6/469 |
| 2020/0008773 A1* | 1/2020 | Vogtmeier | G01N 23/043 |
| 2020/0107799 A1* | 4/2020 | Nebosis | A61B 6/587 |
| 2021/0383514 A1* | 12/2021 | Kitano | A61B 6/487 |
| 2022/0022835 A1* | 1/2022 | Sugahara | A61B 6/589 |

\* cited by examiner

X-RAY DEVICE

CROSS REFERENCE TO RELATED APPLICATION

This application claims priority from and benefit of Korean Patent Application No. 10-2021-0103234, filed on Aug. 5, 2021, which is hereby incorporated by reference for all purposes as if fully set forth herein.

TECHNICAL FIELD

The present disclosure generally relates to an X-ray imaging device, more specifically, an X-ray imaging device configured to acquire a first separation distance between an X-ray radiation focal point of a radiator and a subject and allow or block X-ray radiation of the radiator based on the first separation distance, thereby preventing the radiation of the X-ray without a physical skin guard when the subject approaches within a certain distance from the radiator, and to acquire a second separation distance between the radiator and an X-ray detector and automatically set a strength of the X-ray radiation output based on the thickness of the subject acquired from the first separation distance and the second separation distance, thereby being capable of omitting a process of setting a strength of the X-ray radiation output according to the thickness of the subject.

RELATED ART

In medical technical areas, X-ray imaging devices are widely used as means for acquiring an image of inside of human body.

The X-ray is called as a short-wavelength electromagnetic wave having a specific wavelength range and frequency range, and the X-ray imaging is radiography projecting the X-ray and displaying the inside of a photography object using high permeability of the X-ray.

As well known, X-rays accompany attenuation such as photoelectric effect or Compton scattering, depending on the material, density, and thickness of an object, while penetrating the object. Therefore, X-ray radiography displays a projected image for the inside of the object at a plane gray scale, based on an attenuation amount of X-rays which are accumulated while the X-rays penetrate the object. For this operation, a separate X-ray system is used.

Meanwhile, X-ray imaging devices can be categorized into a fixed hold type being used in general medical purposes and a portable type which is miniaturized to be easily carried. Such a portable X-ray imaging device is used for the X-ray image photographing for animal, and its scope of application is extending to medical purposes or industrial purposes.

Figure 1:
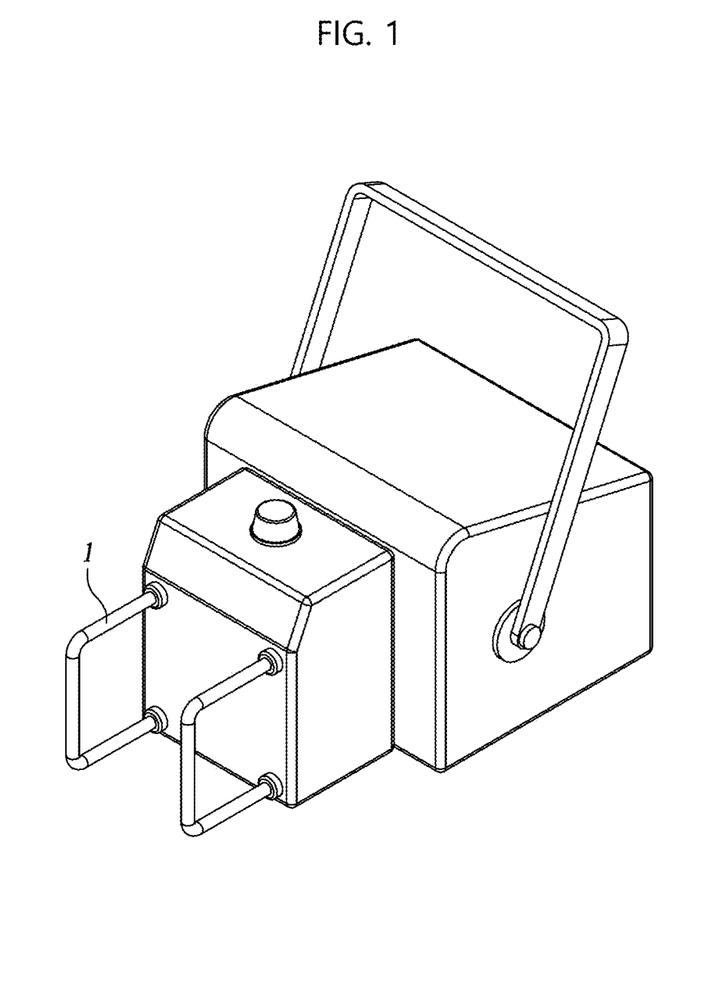
FIG. 1 is a figure for illustrating an X-ray imaging device to which a conventional physical skin guard is mounted.

The X-ray imaging devises are regulated to include means for preventing imaging radiation when a distance between a focal point and skin is less than or equal to a reference distance (e.g. 20 cm). Accordingly, as illustrated in FIG. 1, conventional X-ray imaging devices can prevent physical approach of a subject by attaching a skin guard (1) to a front side of an X-ray radiator so that the subject cannot approach within the reference distance from the focal point.

Accordingly, the conventional skin guard (1) should be manufactured such that a protrusion length in a front side direction of an X-ray radiator exceeds a reference distance (e.g. 20 cm). However, the protrusion length of the skin guard results in increasing the size of the X-ray image device, and specially when the conventional skin guard (1) is applied to a portable type X-ray imaging device required for miniaturization the problem may exist in that its portability can be lowered due to the increase in the size.

RELATED ART DOCUMENT

Patent Document (Patent Document 1) Korean Patent Registration No. 10-2211183

SUMMARY

Technical Problem

To solve the problems of conventional art described above, the purpose of the present disclosure is providing an X-ray imaging device configured to acquire a first separation distance between an X-ray radiation focal point of a radiator and a subject and allow or block X-ray radiation of the radiator based on the first separation distance, thereby preventing the radiation of the X-ray without a physical skin guard when the subject approaches within a certain distance from the radiator.

Another purpose of the present disclosure is providing an X-ray imaging device configured to output warnings different from each other to distinguish between one case that the acquired first separation distance does not reach an appropriate distance range and another case that the acquired first separation distance exceeds an appropriate distance range and to guide to perform X-ray imaging in a state that a subject is positioned within an appropriate distance range from a radiator.

Still another purpose of the present disclosure is providing an X-ray imaging device configured to acquire a second separation distance between the radiator and an X-ray detector and automatically set a strength of the X-ray radiation output based on the thickness of the subject acquired from the first separation distance and the second separation distance, thereby being capable of omitting a process of manually setting a strength of the X-ray radiation output according to the thickness of the subject.

Solution to Problem

An X-ray device according to an embodiment of the present disclosure comprises: a radiator configured to radiate an X-ray; a distance measurement sensor configured to measure a value of a distance to an object; and a controller configured to acquire a first separation distance between an X-ray radiation focal point of the radiator and a subject, and control operation of the radiator based on the acquired first separation distance.

At that time, the controller may comprise: a first separation distance acquiring unit configured to acquire the first separation distance based on the measured value of the distance; and a skin guard unit configured to allow or block X-ray radiation of the radiator based on the acquired first separation distance.

Additionally, the skin guard unit may be configured to: if the first separation distance is greater than a first reference distance, allow the X-ray radiation of the radiator, and if the first separation distance is less than or equal to the first reference distance, block the X-ray radiation of the radiator.

Further, the X-ray device further comprises a warning module configured to output at least one of warning means comprising sound, text, and light, and the controller further comprises a warning output unit configured to, if the first separation distance is less than or equal to the first reference distance, control operation of the warning module such that at least one of the warning means is outputted in a first pattern.

In addition, the warning output unit may be configured to, if the first separation distance is greater than a second reference distance, control operation of the warning module such that at least one of the warning means is outputted in a second pattern, and the second reference distance may be longer than the first reference distance, and the first pattern and the second pattern may be different from each other.

Further, the controller may comprise an output setting unit configured to set a strength of the X-ray radiation output of the radiator based on the first separation distance and a second separation distance between the radiator and an X-ray detector.

Additionally, the controller may further comprise: a first separation distance acquiring unit configured to acquire the first separation distance from the measured value of the distance; a second separation distance acquiring unit configured to acquire the second separation distance; and a subject thickness acquiring unit configured to acquire a value of thickness of the subject based on difference between the acquired first separation distance and the acquired second separation distance, and the output setting unit may be configured to set a strength of the X-ray radiation output in proportion to the acquired value of the thickness of the subject.

In addition, the controller may further comprise an acquisition mode setting unit configured to select and set one mode among a first acquisition mode for acquiring the first separation distance from the measured value of the distance and a second acquisition mode for acquiring the second separation distance from the measured value of the distance, and the acquisition mode setting unit is configured to, if the first acquisition mode is set, control the first separation distance acquiring unit to acquire the first separation distance based on the value of the distance, and, if the second acquisition mode is set, control the second separation distance acquiring unit to acquire the second separation distance based on the value of the distance.

Advantageous Effects of Invention

According to present disclosure, by acquiring a first separation distance between an X-ray radiation focal point of a radiator and a subject and allowing or blocking X-ray radiation of the radiator based on the first separation distance, the radiation of the X-ray can be prevented without a physical skin guard when the subject approaches within a certain distance from the radiator, thereby preventing the increase in the size caused by the installation of the physical skin guard.

Additionally, by outputting warnings different from each other to distinguish between one case that the acquired first separation distance does not reach an appropriate distance range and another case that the acquired first separation distance exceeds an appropriate distance range, the performance of the X-ray imaging can be guided in a state that a subject is positioned within an appropriate distance range from a radiator.

Further, by acquiring a second separation distance between the radiator and an X-ray detector and automatically setting a strength of the X-ray radiation output based on the thickness of the subject acquired from the first separation distance and the second separation distance, a process of manually setting a strength of the X-ray radiation output according to the thickness of the subject can be omitted, thereby improving efficiency of the X-ray imaging and reducing the time for the X-ray imaging.

DETAILED DESCRIPTION OF EMBODIMENTS

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

Hereinafter, with reference to the enclosed drawings, an X-ray imaging device according to an embodiment of the present disclosure is described in detail.

Figure 2:
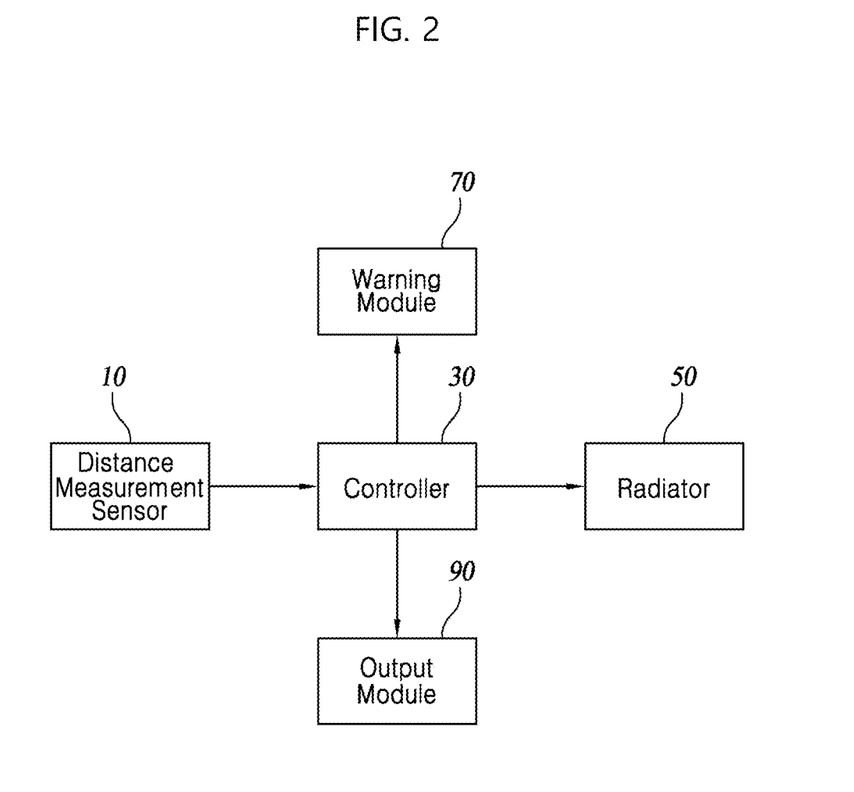
FIG. 2 is a functional block diagram of an X-ray device according to an embodiment of the present disclosure.
Figure 3:
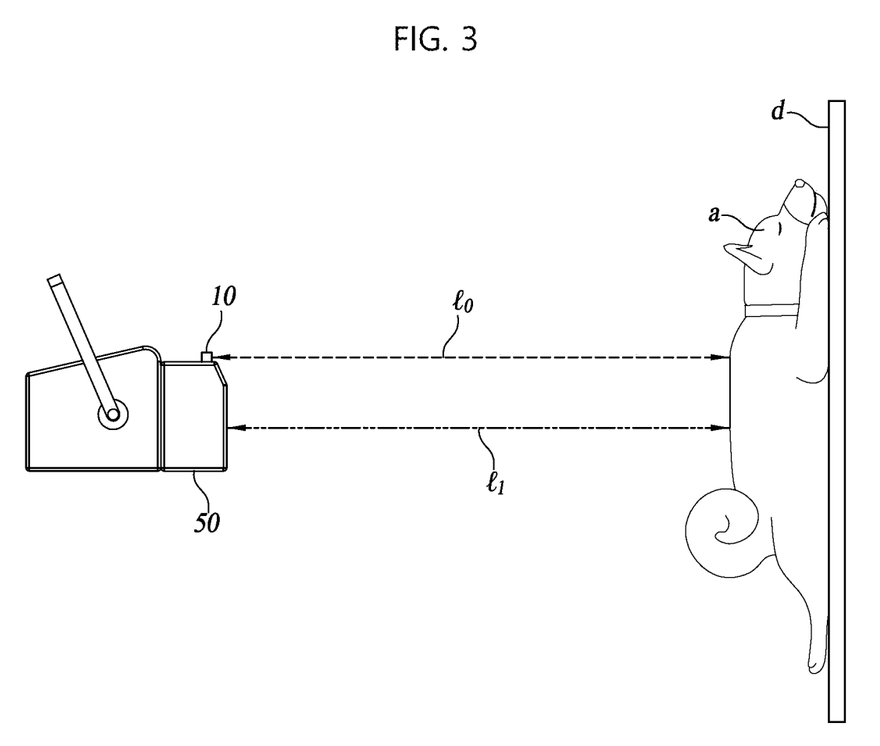
FIG. 3 is a figure for illustrating a process of acquiring a first separation distance of an X-ray device according to an embodiment of the present disclosure.

FIG. 2 is a functional block diagram of an X-ray device according to an embodiment of the present disclosure, and FIG. 3 is a figure for illustrating a process of acquiring a first separation distance of an X-ray device according to an embodiment of the present disclosure.

An X-ray device according to the present application is characterized in preventing from photographing a subject within a certain distance from an X-ray radiation focal point without installing a physical skin guard. Additionally, an X-ray device according to an embodiment is characterized in being capable of automatically setting a strength of the X-ray radiation output according to the thickness of a subject to omit a strength of the X-ray radiation output setting process according to the thickness of the subject.

For the purpose of this, an X-ray device according to the present embodiment comprises a distance measurement sensor (10) configured to measure a value of a distance to an object, a controller configured to control the operation of a radiation unit or radiator (50), and the radiation unit or radiator (50) configured to radiate an X-ray.

Referring to FIG. 2, the distance measurement sensor (10) is disposed adjacent to the radiator (50) and may measure the value of the distance to the object in a direction of X-ray radiation of the radiator (50). At that time, the value of the distance is a separation distance to the object from the distance measurement sensor (10), the distance measurement sensor (10) can be implemented as various types of sensors capable of measuring a distance, and, for example, an infrared sensor, an ultrasonic sensor, a laser sensor, a lidar sensor and so on can be applied thereto.

As illustrated in FIG. 3, after positioning a subject (a) at a X-ray detector (d) for detecting an X-ray radiated from the radiator (50), if distance measurement toward the subject (a) is performed using the distance measurement sensor (10), the measured value of the distance can be a distance value ($I_0$) from a distance measurement sensor to the subject.

The distance value ($I_0$) measured by the distance measurement sensor is provided to a control unit or controller (30). The controller (30) can acquire a first separation distance ($I_1$) from the distance value ($I_0$) provided by the distance measurement sensor. Here, the first separation distance ($I_1$) may mean a separation distance from an X-ray radiation focal point of the radiator (50) to the subject as illustrated in FIG. 3.

The controller (30) can acquire the first separation distance ($I_1$) by adding or subtracting a calibration distance from an X-ray radiation focal point of the radiator (50) to the distance measurement sensor (10) to or from the distance value ($I_0$) provided by the distance measurement sensor. Here, the calibration distance may be a distance with respect to an X-ray radiating direction, and, if the distance measurement sensor (10) is arranged on the same line as the X-ray radiation focal point of the radiator (50) with respect to the X-ray radiating direction, the measured distance value ($I_0$) and the first separation distance ($I_1$) may be equal to each other. Accordingly, when the distance measurement sensor (10) is arranged on the same line as the X-ray radiation focal point of the radiator (50) so that the distance value ($I_0$) and the first separation distance ($I_1$) can be equal to each other, the controller (30) can omit a separate process for acquiring the first separation distance ($I_1$) and can determine the distance value ($I_0$) provided by the distance measurement sensor (10) as the first separation distance ($I_1$).

The controller (30) can allow or block X-ray radiation of the radiator (50) based on the first separation distance.

If operation for X-ray radiation (or filament preheat) is manipulated by a user in a state that the controller (30) allows the X-ray radiation, the radiator (50) can perform the X-ray radiation (or filament preheat). However, if the controller (30) blocks the X-ray radiation, user's manipulation for the X-ray radiation (or filament preheat) is physically blocked, or a manipulation signal is not transmitted to the radiator (50) even when the user manipulates the X-ray device for the X-ray radiation (or filament preheat), or the radiator (50) may not perform the X-ray radiation (or filament preheat) even when the manipulation signal for the X-ray radiation (or filament preheat) is transmitted to the radiator (50). Further detailed explanation regarding allowance/block of X-ray radiation of the controller (30) will be described below with reference to FIGS. 4 to 5.

The controller (30) may allow or block the X-ray radiation of the radiator (50) based on the first separation distance, and may acquire a value of thickness of the subject and automatically set an X-ray output of the radiator (50) based on the thickness value of the subject. At that time, the value of thickness of the subject may mean a value of thickness in a direction of X-ray penetration of the subject, and parameters of the controller (30) for setting an X-ray output may comprise a tube voltage (kV), a tube current (mA, mAs), and so on. Here, a process of acquiring a value of thickness of a subject by the controller and a process of setting an X-ray output accordingly will be described below with reference to FIG. 4 as well as FIGS. 6 to 7.

The X-ray device according to the present disclosure may allow or block X-ray radiation according to the first separation distance as well as may warn the user whether a current first separation distance is an appropriate distance or output the current first separation distance so that the user can monitor the current first separation distance.

For this, the X-ray device according to the present embodiment may comprise a warning module (70) configured to output an warning according to the first separation distance and an output module (90) configured to visually display the first separation distance as illustrated in FIG. 2.

The warning module (70) can output any one of warning means such as sound, text, and light, and output the warning means in various patterns. For example, when the warning means outputted by the warning module (70) is beat sound, short beat sound may be repeatedly outputted at short time intervals or long beat sound may be repeatedly outputted at long time intervals. At this time, the operation of the warning module (70) is controlled by the controller (30), and the pattern of being outputted as the warning means can be also determined by the controller (30).

The output module (90) visually outputs the first separation distance acquired by the controller (30) in real time so that user can monitor the first separation distance in real time. Therefore, the user can appropriately adjust a distance between the X-ray radiation focal point of the radiator (50) and the subject (a) while checking an output value being outputted by the output module (90). The operation of the output module (90) can be also controlled by the controller (30).

Figure 4:
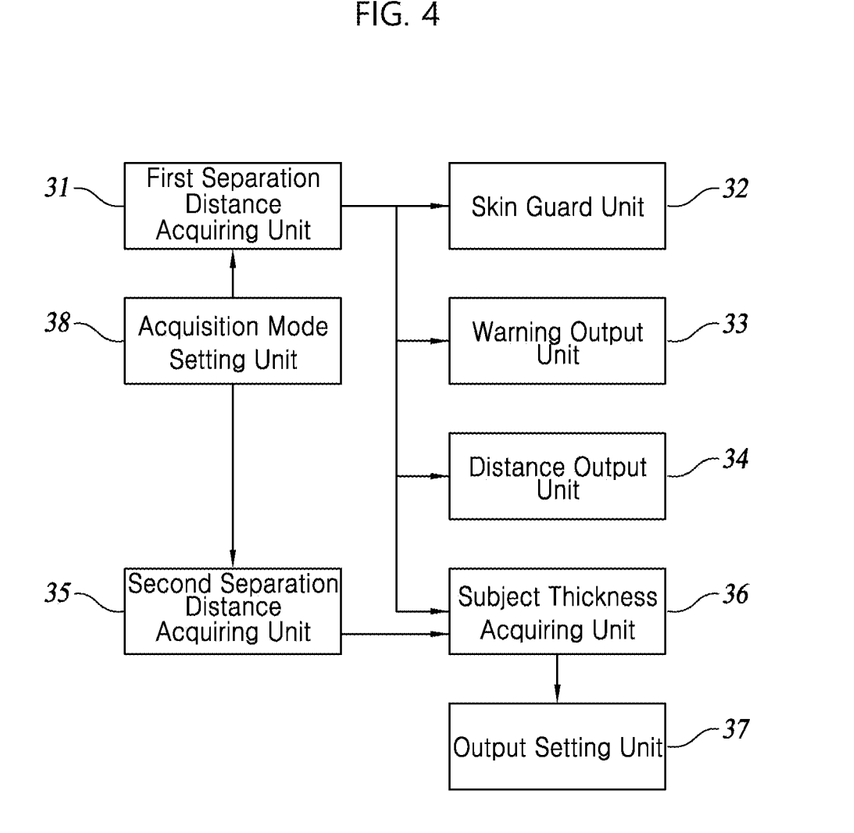
FIG. 4 is a functional block diagram of a controller according to an embodiment of the present disclosure.
Figure 5:
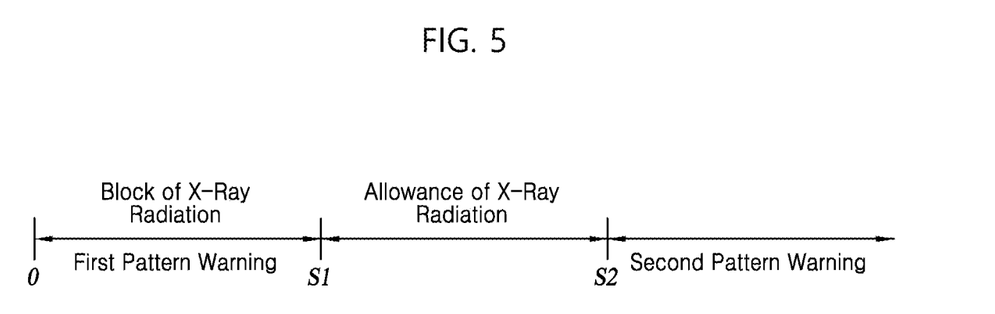
FIG. 5 is a figure for illustrating a control feature of each range of a first separation distance of a controller according to an embodiment of the present disclosure.
Figure 6:
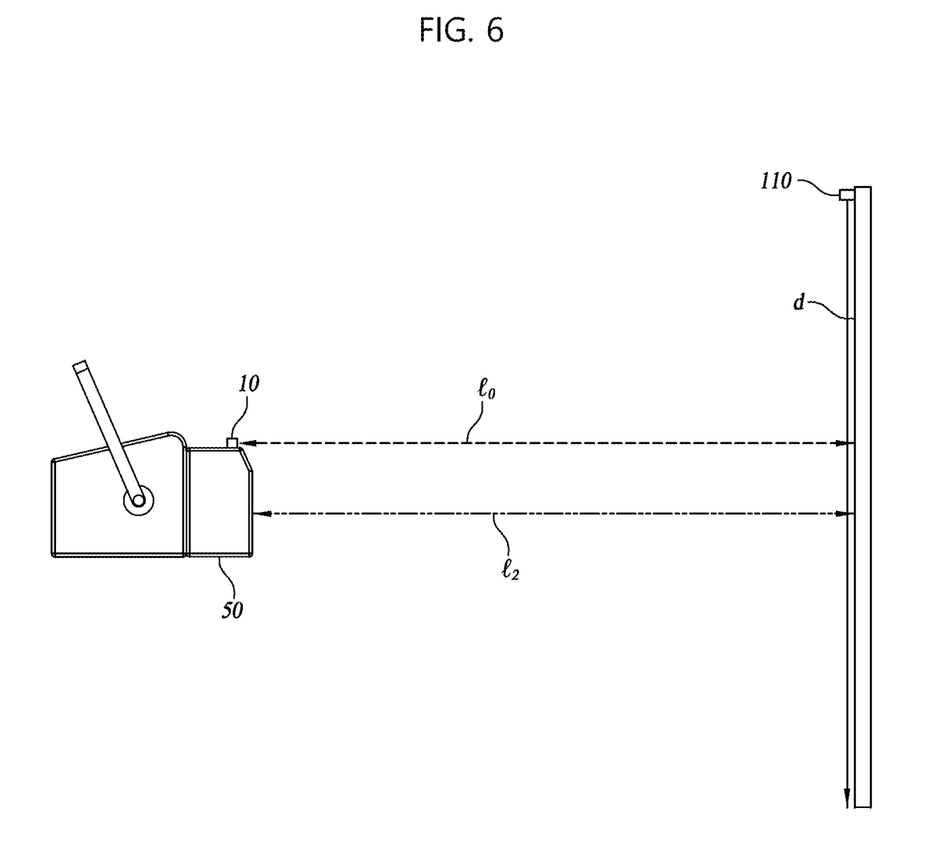
FIG. 6 is a figure for illustrating a process of acquiring a second separation distance of an X-ray device according to an embodiment of the present disclosure.
Figure 7:
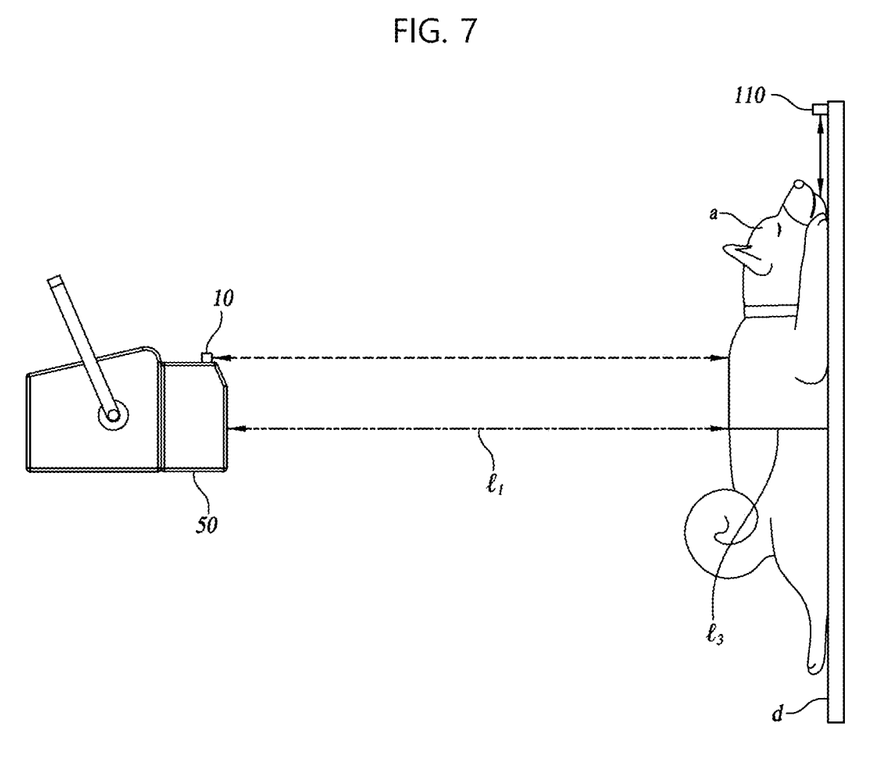
FIG. 7 is a figure for illustrating a process of acquiring a value of thickness of a subject of an X-ray device according to an embodiment of the present disclosure.

FIG. 4 is a functional block diagram of a controller according to an embodiment of the present disclosure, FIG. 5 is a figure for illustrating a control feature of each range of a first separation distance of a controller according to an embodiment of the present disclosure, and FIG. 6 is a figure for illustrating a process of acquiring a second separation distance of an X-ray device according to an embodiment of the present disclosure. And, FIG. 7 is a figure for illustrating a process of acquiring a value of thickness of a subject of an X-ray device according to an embodiment of the present disclosure.

As described above, the controller (30) acquires the first separation distance, and can allow or block the X-ray radiation of the radiator (50) based on the acquired first separation distance. Additionally, the controller (30) can warn the user whether a current first separation distance is an appropriate distance using the warning module (70), or can output a current first separation distance using the output module so that the user can monitor the current first separation distance.

For this, the controller (30) can be configured to comprise a first separation distance acquiring unit (31) configured to acquire the first separation distance, a skin guard unit (32) configured to allow or block the X-ray radiation of the radiator (50), a warning output unit (33) configured to control the operation of the warning module (70), and a distance output unit (34) configured to control the operation of the output module (90).

The first separation distance acquiring unit (31) can acquire the first separation distance by adding or subtracting a calibration distance from an X-ray radiation focal point of the radiator (50) to the distance measurement sensor (10) to or from a value of distance provided by the distance measurement sensor (10). The first separation distance acquired by the first separation distance acquiring unit (31) is provided to the skin guard unit (32), and the skin guard unit (32) can allow or block the X-ray radiation of the radiator based on the provided first separation distance.

Specifically, the skin guard unit (32) is configured to, if the provided first separation distance is greater than a first reference distance, allow the X-ray radiation of the radiator, and, if the first separation distance acquired by the first separation distance acquiring unit (31) is less than or equal to the first reference distance, block the X-ray radiation of the radiator. At that time, the first separation distance can be set to 20 cm, but not limited thereto.

Accordingly, the X-ray device according to the present embodiment controls not to radiate the X-ray when the first separation distance between the X-ray radiation focal point and the subject is less than or equal to the first reference distance so that close-up within the first reference distance of the subject can be prevented without installing a physical skin guard, and therefore increase in volume which results from installing a physical skin guard can be prevented.

The first separation distance acquired from the first separation distance acquiring unit (31) can be provided to the skin guard unit (32) as well as the warning output unit (33) and the distance output unit (34).

The warning output unit (33) can control the operation of the warning module (70) based on the first separation distance provided from the first separation distance acquiring unit (31). Specifically, when the first separation distance acquired by the first separation distance acquiring unit (31) is less than or equal to a first reference distance, the warning output unit (33) controls the operation of the warning module (70) such that the warning means can be outputted in a first pattern, and when the first separation distance acquired by the first separation distance acquiring unit (31) is greater than a second reference distance, the warning output unit (33) controls the operation of the warning module (70) so that the warning means can be outputted in a second pattern. For example, the second reference distance may be longer than the first reference distance, and the first pattern and the second pattern may be different from each other.

As examples of the first pattern and the second pattern, the first pattern can be a pattern in which short beat sound is outputted at short time intervals, and the second pattern can be a pattern in which long beat sound is outputted at long time intervals. Accordingly, by differentiating between a output pattern outputted by the warning module (70) when the first separation distance is less than or equal to the first reference distance and a output pattern outputted by the warning module (70) when the first separation distance is greater than the second reference distance, the user can recognize whether a warning outputted from the warning module (70) is warning sound outputted because a current first separation distance is too close or warning sound outputted because a current first separation distance is too far, and therefore, an X-ray device according to the present embodiment can guide so that X-ray imaging can be performed in a state that a subject is positioned within an appropriate distance range from an X-ray radiation focal point of the radiator (50).

Referring to FIG. 5, when the first separation distance acquired by the first separation distance acquiring unit (31) is less than or equal to a first reference distance (S1), the skin guard unit (32) blocks the X-ray radiation of the radiator (50) and the warning output unit (33) controls the operation of the warning module (70) to output warning of the first pattern.

If the first separation distance acquired by the first separation distance acquiring unit (31) is greater than the first reference distance (S1) and less than or equal to a second reference distance (S2), the skin guard unit (21) can permit the X-ray radiation of the radiator (50). At that time, the warning of the warning module (70) may not be outputted.

However, if the first separation distance acquired by the first separation distance acquiring unit (31) is greater than the second reference distance (S2), the warning output unit (33) controls the operation of the warning module (70) so as to output warning of the second pattern. At that time, the skin guard unit (32) can block the X-ray radiation, but alternatively the skin guard unit (32) can allow the X-ray radiation. The block/allowance of the X-ray radiation of the skin guard unit (32) when the first separation distance exceeds the second reference distance (S2) can be determined according to a set option set by a user.

The distance output unit (34) can control the operation of the output module (90) so as to output the provided first separation distance. At that time, the output module (90) makes visualizing the first separation distance and outputs it according to the control of the distance output unit (34), but it can be outputted by variously changing an outputted number or background color. Preferably, if the provided first separation distance is less than or equal to the first reference distance, the distance output unit (34) controls the operation of the output module (90) so that a number or background of first color (for example, red) is outputted, if the provided first separation distance is greater than the first reference distance and less than or equal to the second reference distance, the distance output unit (34) controls the operation of the output module (90) so that a number or background of second color (for example, green) is outputted, and if the provided first separation distance is greater than the second reference distance, the distance output unit (34) controls the operation of the output module (90) so that a number or background of third color (for example, orange) is outputted Meanwhile, as described above, the controller (30) can allow or block the X-ray radiation of the radiator (50) based on the first separation distance as well as can acquire a value of thickness of a subject and automatically set X-ray output of the radiator based on the value of thickness of the subject.

For this, as illustrated in FIG. 4, the controller (30) is configured to further comprise a second separation distance acquiring unit (35) configured to acquire a second separation distance, a subject thickness acquiring unit (36) configured to acquire a value of thickness of a subject, and a output setting unit (37) configured to automatically set X-ray radiation output of the radiator (50).

The second separation distance acquiring unit (35) can acquire the second separation distance. Here, the second separation distance may mean a distance from a X-ray radiation focal point of the radiator (50) to an X-ray detector (d). In an X-ray device according to the present embodiment, when the radiator (50) and the X-ray detector (d) are fixed, the second separation distance can be a fixed value. However, when the position of the radiator (50) or the X-ray detector (d) can be changed or an X-ray device according to the present embodiment is a portable X-ray device, the second separation distance can be varied.

Like this, when the second separation distance can be varied, the second separation distance acquiring unit (35) can acquire a second separation distance ($I_2$) from a distance value ($I_0$) measured toward the X-ray detector (d) by the distance measurement sensor in a state that a subject is not arranged at the X-ray detector (d) as illustrated in FIG. 6. At that time, the distance value ($I_0$) measured by the distance measurement sensor is a separation distance between the distance measurement sensor (10) and the X-ray detector (d), and the second separation distance acquiring unit (35) receiving the distance value ($I_0$) measured by the distance measurement sensor can acquire the second separation distance ($I_2$) by adding or subtracting a calibration distance from a X-ray radiation focal point of the radiator (50) to the distance measurement sensor (10) to or from the provided distance value ($I_0$).

The second separation distance ($I_2$) acquired by the second separation distance acquiring unit (35) can be provided to the subject thickness acquiring unit (36). And, the subject thickness acquiring unit (36) can be provided with the first separation distance ($I_1$) acquired by the first separation distance acquiring unit (31) as well.

The subject thickness acquiring unit (36) to which the first separation distance ($I_1$) and the second separation distance ($I_2$) are provided can be configured to acquire a value of thickness of the subject from the acquired second separation distance and first separation distance. Typically, as illustrated in FIG. 7, the X-ray imaging is performed in a state that the subject (a) contacts, or is positioned to be close to, the X-ray detector (d) during the X-ray imaging. Accordingly, the subject thickness acquiring unit (36) can acquire a subject thickness value ($I_3$) by subtracting the provided first separation distance ($I_1$) from the provided second separation distance ($I_2$).

The value of thickness of the subject acquired by the subject thickness acquiring unit (36) can be provided to the output setting unit (37). The output setting unit (37) can set the X-ray radiation output of the radiator based on the provided value of thickness of the subject. Specifically, the output setting unit (37) can set the strength of the radiation output such that a tube voltage or tube current is increased in proportion to the acquired value of thickness of the subject.

Therefore, the X-ray device according to the present disclosure may have a technical effect in that the easiness of the X-ray imaging can be improved and the time for the X-ray imaging can be reduced by automatically setting the X-ray radiation output based on a subject thickness, thereby being able to omit a manual process of setting a strength of the X-ray radiation output according to a penetration direction thickness of the subject.

Both the first separation distance acquiring unit (31) and the second separation distance acquiring unit (35) acquire the first separation distance or the second separation distance by receiving a distance value measured by the distance measurement sensor (10). Specifically, when the distance measurement sensor (10) measures a separation distance between the distance measurement sensor (10) and the subject, the first separation distance acquiring unit (31) acquires the first separation distance through the measured value of the separation distance, and, when the distance measurement sensor (10) measures a separation distance between the distance measurement sensor (10) and the X-ray detector (d), the second separation distance acquiring unit (35) acquires the second separation distance through the measured value of the separation distance. Accordingly, the controller (30) determines whether the distance value measured by the distance measurement sensor (10) is the separation distance between the distance measurement sensor (10) and the subject or whether the distance value measured by the distance measurement sensor (10) is the separation distance between the distance measurement sensor (10) and the X-ray detector (d), and selects to whether to acquire the first separation distance or to acquire the second separation distance through the distance value measured by the distance measurement sensor (10).

For this, as illustrated in FIG. 4, the controller (30) may be configured to further comprise an acquisition mode setting unit (38). The acquisition mode setting unit (38) can set an acquisition mode by selecting one mode among a first acquisition mode acquiring the first separation distance from the distance value provided from the distance measurement sensor (10) and a second acquisition mode acquiring the second separation distance from the measured distance value.

If the first acquisition mode is set by the acquisition mode setting unit (38), the first separation distance acquiring unit (31) acquires the first separation distance based on the provided distance value, and, if the second acquisition mode is set by the acquisition mode setting unit (38), the second separation distance acquiring unit (35) acquires the second separation distance based on the provided distance value. Accordingly, the X-ray device according to the present embodiment can be configured to acquire the first separation distance if the distance measurement sensor (10) measures a distance value in a state that the first acquisition mode is selected and set, and to acquire the second separation distance if the distance measurement sensor (10) measures a distance value in a state that the second acquisition mode is selected and set.

At that time, the acquisition mode setting unit (38) can select an acquisition mode according to an input of the user, or select an acquisition mode based on subject detection information received from an outside of the X-ray device.

When the acquisition mode setting unit (38) selects an acquisition mode according to the input of the user, the user can input to decide one of the first acquisition mode or the second acquisition mode according to whether the subject is disposed at the X-ray detector.

When the acquisition mode setting unit (38) selects an acquisition mode based on the subject detection information received from the outside of the X-ray device, a subject detection sensor (110) may be installed. As illustrated in FIG. 6 or 7, the subject detection sensor (110) may be disposed at and protrude from one side end portion of the X-ray detector (d), and can detect whether the subject is disposed at one side of the X-ray detector (d). Here, the subject detection sensor (110) can be implemented with various sensors which can detect whether an object exists within a certain distance, and an ultra-sound sensor, an infrared sensor, a laser sensor, a lidar sensor and so on can be used.

When the subject detection sensor (110) is installed, the subject detection information detected by the subject detection sensor (110) can be provided to the acquisition mode setting unit (38) of the controller (30), and, for this, the subject detection sensor (110) and the controller (30) can be wiredly or wirelessly connected to each other.

If the subject detection sensor (110) does not detect the subject as illustrated in FIG. 6, the acquisition mode setting unit (38) selects and sets the first acquisition mode to acquire the first separation distance ($I_1$) from the distance value ($I_0$) measured by the distance measurement sensor, and, if the subject detection sensor (110) detects the subject as illustrated in FIG. 7, the acquisition mode setting unit (38) selects and sets the second acquisition mode to acquire the second separation distance ($I_2$) from the distance value ($I_0$) measured by the distance measurement sensor.

Accordingly, the X-ray device according to the present embodiment can correctly distinguish between the first separation distance and the second separation distance based on the distance value measured by the distance measurement sensor (10) without the user's input for mode selection.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes. Accordingly, the scope of the disclosure is not to be limited by the above embodiments but by the claims and the equivalents thereof.

REFERENCE CHARACTERS OF DRAWINGS

10: Distance Measurement Sensor
30: Controller
31: First Separation Distance Acquiring Unit
32: Skin Guard Unit
33: Warning Output Unit
34: Distance Output Unit
35: Second Separation Distance Acquiring Unit
36: Subject Thickness Acquiring Unit
37: Output Setting Unit
38: Acquisition Mode Setting Unit
50: Radiator
70: Warning Module
90: Output Module
110: Subject Detection Sensor

What is claimed is:

1. An X-ray device comprising: a radiator configured to radiate an X-ray;
an X-ray detector configured to detect the X-ray radiated by the radiator;
a distance measurement sensor configured to measure values of a distance to a subject in a first acquisition mode and a second acquisition mode; and
a controller processor configured to;
acquire a first separation distance between an X-ray radiation focal point of the radiator and the subject based on the value of the distance measured in the first acquisition mode, and control operation of the radiator based on the acquired first separation distance,
wherein the controller processor is configured to:
acquire a second separation distance between the X-ray radiation focal point of the radiator and an X-ray detector based on the value of the distance measured in the second acquisition mode, and
acquire subject detection information detected by a subject detection sensor comprised in the X-ray detector, and select one mode among the first acquisition mode and the second acquisition mode based on the acquired subject detection information.

2. The X-ray device according to claim 1, wherein the controller processor is configured to:
acquire the first separation distance based on the measured value of the distance; and
allow or block X-ray radiation of the radiator based on the acquired first separation distance.

3. The X-ray device according to claim 1, wherein the controller processor is configured to set a strength of the X-ray radiation output of the radiator based on the first separation distance and the second separation distance between the radiator and the X-ray detector.

4. The X-ray device according to claim 2, wherein the controller processor is configured to:
if the first separation distance is greater than a first reference distance, allow the X-ray radiation of the radiator, and
if the first separation distance is less than or equal to the first reference distance, block the X-ray radiation of the radiator.

5. The X-ray device according to claim 4, wherein the controller processor is configured to, if the first separation distance is less than or equal to the first reference distance, control to output at least one of the warning means comprising sound, text, and light in a first pattern.

6. The X-ray device according to claim 5, wherein:
the controller processor is configured to, if the first separation distance is greater than a second reference distance, control to output at least one of the warning means in a second pattern, and
the second reference distance is longer than the first reference distance, and the first pattern and the second pattern are different from each other.

7. The X-ray device according to claim 3, wherein the controller processor is configured to:
acquire a value of thickness of the subject based on difference between the acquired first separation distance and the acquired second separation distance, and wherein the controller processor is configured to set a strength of the X-ray radiation output in proportion to the acquired value of the thickness of the subject.

8. The X-ray device according to claim 7, wherein:
the controller processor is configured to:
if the first acquisition mode is set, control to acquire the first separation distance based on the value of the distance, and, if the second acquisition mode is set, control to acquire the second separation distance based on the value of the distance.

* * * * *